United States Patent [19]

Rose

[11] Patent Number: 4,777,745
[45] Date of Patent: Oct. 18, 1988

[54] TOOTH STORAGE AND DISPLAY APPARATUS

[76] Inventor: Carolyn A. Rose, 30461 227th Pl. SE., Kent, Wash. 98042

[21] Appl. No.: 787,491

[22] Filed: Oct. 15, 1985

[51] Int. Cl.$^4$ ............................................. A47G 1/06
[52] U.S. Cl. ..................................................... 40/152
[58] Field of Search .................... 206/83, 475, 533; 40/152, 160

[56] References Cited

U.S. PATENT DOCUMENTS

| | | | |
|---|---|---|---|
| 1,310,729 | 7/1919 | Appelbee | 206/475 |
| 1,940,328 | 12/1933 | Schrotenboer | 40/152 |
| 2,102,519 | 12/1937 | Cross | 40/152 |
| 2,288,909 | 7/1942 | Low | 206/83 |
| 2,536,645 | 1/1951 | Johnson et al. | 40/152 |
| 3,283,431 | 11/1966 | Pearlman | 40/152 |
| 4,117,613 | 10/1978 | Hosker | 40/152.1 |
| 4,158,266 | 6/1979 | Gilmour | 40/152 |
| 4,222,188 | 9/1980 | Tarrant et al. | 40/152.1 |
| 4,244,303 | 1/1981 | Kurasik | 40/152 |
| 4,261,122 | 4/1981 | Le Vine | 40/152 |

FOREIGN PATENT DOCUMENTS 847982 8/1952 Fed. Rep. of Germany ........ 40/160

Primary Examiner—Gene Mancene
Assistant Examiner—Cary E. Stone

[57] ABSTRACT

The subject invention is a picture frame adapted to contain, in addition to a picture, apparatus for storing and displaying teeth. The apparatus are accessible from the back of the frame and comprise a component having indentations for holding the teeth as well as for holding various items usable in the enactment of the tooth fairy myth. The items include containers for a tooth and for the coins to be exchanged for the tooth. The componet having indentations is covered by a removable transparent layer which in turn is covered by a back cover. The back cover may have an openable/closable or removable portion for display of the stored items or it may be readily removable for such display.

3 Claims, 2 Drawing Sheets

TOOTH STORAGE AND DISPLAY APPARATUS

BACKGROUND OF THE INVENTION

1. Field of the Invention

The subject invention is in the field of storage apparatus and particularly of such apparatus in which the stored items may be displayed. Still more particularly, the items may be concealed or displayed and a factor relating to the concealment is that the apparatus does not appear to be a storage apparatus.

2. Prior Art

A preliminary search related to the subject invention produced the following U.S. Pats. Nos.: 215,221; 2,449,204; 2,218,409; 2,593,195; 2,318,850; 3,743,085; Des. 231,299.

All these patents show apparatus for storing and/or displaying various items such as coins, photographs and medical tablets. The apparatus of U.S. Pat. No. 215,221 provided for storing more photographs than are displayed at any one time with means for selecting those to be displayed. However, all of the patented inventions are identifiable by their appearances as apparatus for displaying the items displayed. None of them provide means for storing and displaying one type of item while appearing to be means for displaying another, such as a photograph or picture.

Accordingly it is an objective of the subject invention to provide means for storing and displaying a first type of item while appearing to be means for displaying a second type. A further objective is that the first type of item be teeth, such as the baby teeth of a particular child, and that the second type of item be a photograph, such as a photograph of the mother of the child. Another objective is that the display of the teeth be optional and, still further, that the display include information relating to the stored teeth.

SUMMARY OF THE INVENTION

The subject invention comprises a specialized picture frame and components which are held in the frame in layered arrangement. The components in layer form comprise, starting at the front of the frame and working back, a transparent layer made of glass or plastic; a mat; a photograph; a layer of backing material for the photograph; a layer having indentations for holding teeth and apparatus useful in the enactment of the tooth fairy myth; a layer, such as a sheet of paper, on which various designs and information are imprinted and to which a photograph may be attached; a second transparent layer; and a back cover. The back cover may have a portion movable or removable to allow viewing the stored teeth through the second transparent layer. Means are provided for integrating the assembly and allowing for simple disassembly of the apparatus for the purposes of using the apparatus for enactment of the tooth fairy myth, for inserting or removing teeth and for recording information on the imprinted layer.

DETAILED DESCRIPTION OF THE INVENTION

Figure 1:
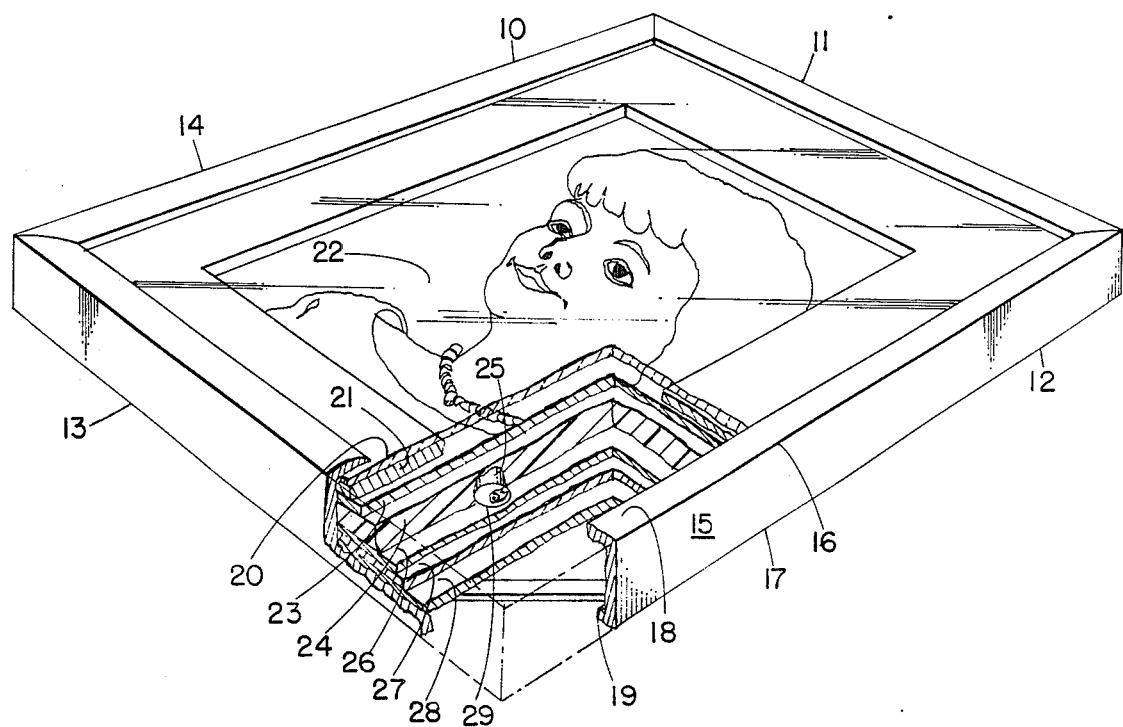
FIG. 1 is a sectional perspective view of the subject invention.

Referring to FIG. 1, the invention comprises a frame 10 of a commercially available type made of extruded aluminum parts 11, 12, 13 and 14 attached to each other using the commercially available connectors for such frames (not shown). The extruded parts each have a side portion 15 with edges 16 and 17. A relatively wide flange 18 extends at right angles to the side portion from edge 16 and a relatively narrow flange 19 extends from edge 17 at right angles to the side portion and in the same direction as flange 18. The wider flanges comprise the front of the frame and the narrower flanges comprise the back. Contents to be held in the frame are inserted through the opening formed by the four flanges 19. This design and construction are well known in the art and frames of this design and construction are commercially available. The subject invention lies in the contents to be held in the frame.

Figure 2:
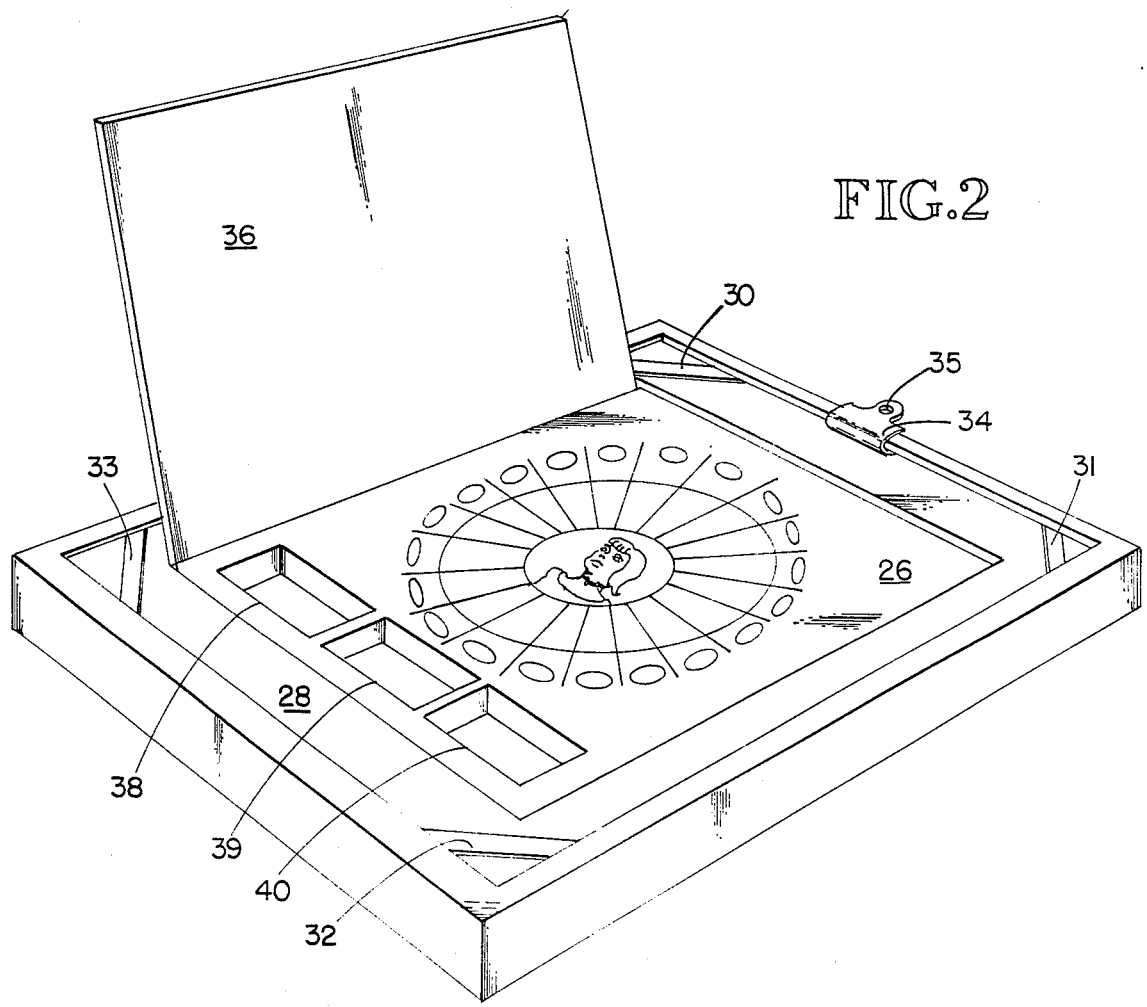
FIG. 2 is a second perspective view showing the means for retaining the contents of the frame in the frame, for hanging the invention on a hook and for showing stored items under display along with information relating to the stored items.

The contents comprise a transparent sheet 20, a mat 21, a photograph 22, a layer of material 23 to back up the photograph, a layer component 24 having indentations in its broad face of which indentation 25 is an example, a layer of paper or equivalent 26, a second transparent layer 27 and a back cover layer 28. The back cover is optional. Layer 26 has apertures which correspond to the openings of the indentations in components 24, aperture 29 being an example. The indentations are open toward the back of the frame. All of the contents are of a size and shape allowing them to pass through the opening in the back of the frame and to not pass through the opening in the front of the frame. They are held in place by flat springs 30, 31, 32 and 33, as shown in FIG. 2. The springs are slightly bowed and as a result have concave and convex sides. They are installed convex side to the contents and with each of their ends caught between the contents and a flange 19. These springs and their use to retain the contents of a picture frame are well known in the art. Clip 34 hooks under a flange 19 and has a hole 35 which can be placed over a hook to hang the picture frame on a wall or the like.

Figure 3:
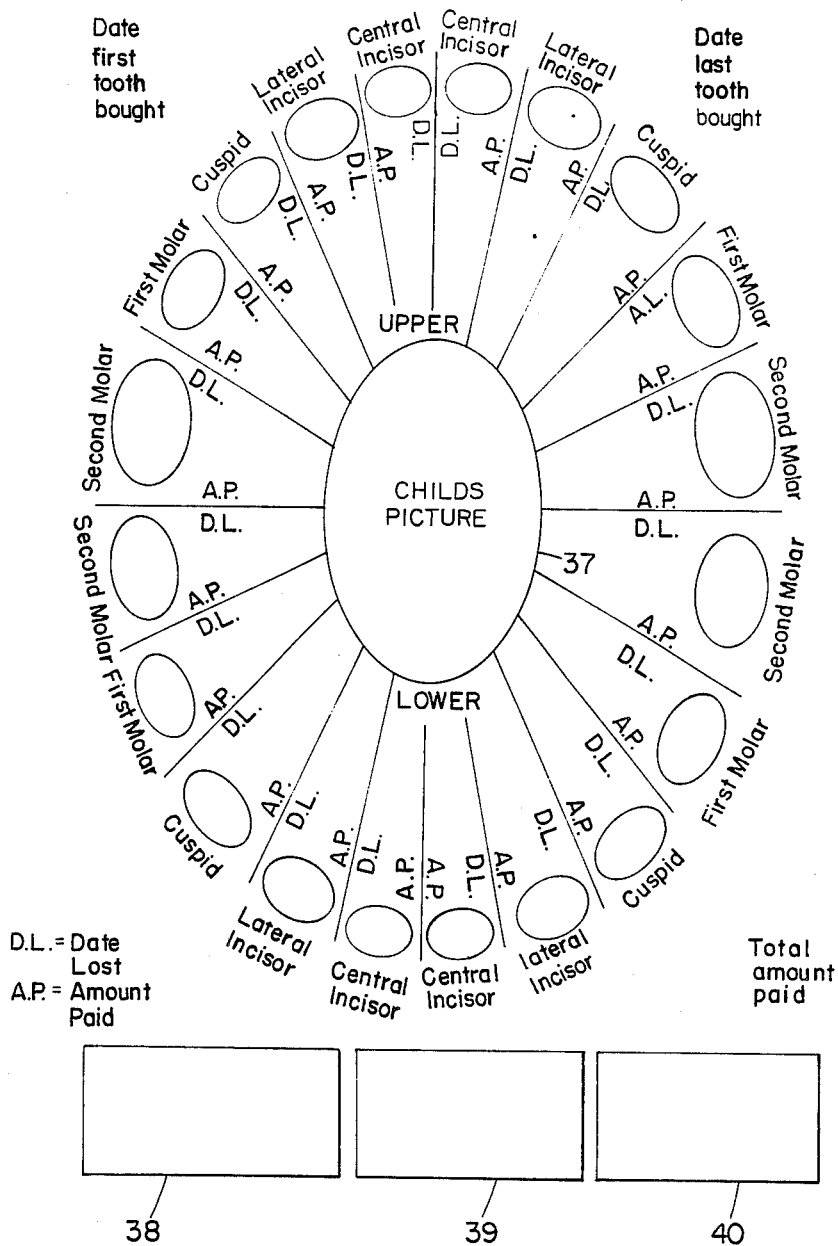
FIG. 3 illustrates a preferred arrangement of the stored items and format for the information related to the stored items.

FIG. 2 illustrates a preferred arrangement for the indentations and preferred format of information on layer 26 for storing and displaying the baby teeth of a child. In this view back cover 28 incorporates a hinged portion 36 which is openable and shown open in order to display the stored teeth and the information related to them. FIG. 3 illustrates the indentation arrangement and information format in more detail. The indentations are arranged elliptically, the upper half representing the teeth from the child's upper jaw and the lower half representing those of the lower jaw. A photograph of the child may be placed behind the oval opening 37 in the center of component 26 or a photograph, preferably oval shaped, can be attached to layer 26.

Near the bottom of the frame are indentations 38, 39 and 40 in component 24 for items used in the enactment of the tooth fairy myth. Indentations 38 and 40 are for receptacles in which a tooth may be placed to be put under the child's pillow and in which the coins to be "left" by the fairy for the tooth may be placed. The receptacle containing the tooth is replaced by the receptacle containing the coins as the child sleeps. Receptacle 39 is for supplies of fairy dust to be sprinkled on the coins to add to the interest and excitement of the enactment.

It may be understood from the drawings and description that the subject invention meets its objectives. One type of item, such as teeth, can be stored in the apparatus and displayed when desired. However, this storage capability is not discernible from the appearance of the apparatus since it appears to be an apparatus for displaying a picture. That is, it appears to be a picture frame with a picture on display. In particular, the stored items may be baby teeth of a child and the picture a picture of the child's mother. Further, the tooth display includes information relating to the teeth.

While a preferred embodiment of the invention is described herein, it will be understood by those skilled in the art that other embodiments or variations of the described embodiment are possible within the scope of the invention, the scope being defined by the attached claims.

What is claimed is:

1. A storage and display apparatus comprising:
   a picture frame having a front and back and adapted to receive and contain a plurality of components in layer form, said components comprising:
   a first transparent layer,
   a picture,
   a component having a broad face and indentations into said face, said indentations having openings in said broad face,
   a component in layer form having a first face and openings through said component in layer form corresponding to said openings in said broad face and having information and a design imprinted on said first face,
   a second transparent layer,
   means for retaining said components in said frame, said components being arranged in said frame in the order listed with said first transparent layer closest to said front,
   said picture facing said front and said broad surface and said first face facing said back.

2. The apparatus of claim 1, further comprising:
   an opaque component in layer form,
   said opaque component being positioned between said second transparent layer and said back.

3. The apparatus of claim 2 in which said opaque component has a hinged portion whereby said portion may be moved to provide an opening in said opaque component through which said indentations can be seen through said second transparent layer.

* * * * *